United States Patent [19]

Sheng et al.

[11] 4,147,884

[45] Apr. 3, 1979

[54] LIQUID PHASE OXIDATION OF UNSATURATED ALDEHYDES TO CORRESPONDING ACIDS

[75] Inventors: Ming N. Sheng; Jar-Lin Kao, both of Cherry Hill, N.J.

[73] Assignee: Atlantic Richfield Company, Los Angeles, Calif.

[21] Appl. No.: 679,958

[22] Filed: Apr. 26, 1976

Related U.S. Application Data

[63] Continuation-in-part of Ser. No. 600,174, Jul. 29, 1975, abandoned.

[51] Int. Cl.$^2$ .................. C07C 51/32; C07C 57/04
[52] U.S. Cl. .................................................. 562/533
[58] Field of Search .......................... 260/530 N, 413

[56] References Cited

U.S. PATENT DOCUMENTS

| 2,153,406 | 4/1939 | Bauer .............................. 260/530 N |
| 2,386,365 | 10/1965 | Peter et al. ...................... 260/530 N |

*Primary Examiner*—Vivian Garner
*Attorney, Agent, or Firm*—John C. Martin, Jr.

[57] ABSTRACT

Process for the liquid phase oxidation of an unsaturated lower aliphatic aldehyde to the corresponding carboxylic acid wherein the oxidation is carried out by passage of an oxygen-containing gas through a liquid medium containing the unsaturated aldehyde and a fluorine-containing organic compound.

15 Claims, No Drawings

LIQUID PHASE OXIDATION OF UNSATURATED ALDEHYDES TO CORRESPONDING ACIDS

RELATED APPLICATIONS

This is a continuation-in-part application of U.S. Ser. No. 600,174, filed July 29, 1975, and now abandoned.

BACKGROUND OF THE INVENTION

Although saturated aldehydes can be relatively easily oxidized to carboxylic acids, it is generally recognized that the oxidation of an unsaturated aldehyde to the corresponding carboxylic acid is accompanied by undesirable side reactions that reduce yield. In particular, it has been difficult to prepare methacrylic acid from methacrolein, an unsaturated aldehyde, in good yield. Whereas a saturated aliphatic aldehyde can generally be converted without difficulty to the corresponding carboxylic acid in high yield, this does not apply to unsaturated aldehydes. One of several problems encountered with the oxidation of unsaturated aldehydes to the corresponding acids is polymerization through the olefinic unsaturation and another problem is that of side reactions or of degradation of the materials present during the reaction with the result that less desirable by-products are formed. The use of conventional polymerization inhibitors is a possible method of restricting such polymerization; but generally these inhibitors are also well known antioxidants and therefore also inhibit the oxidation reaction.

It is known that an unsaturated aliphatic aldehyde can be oxidized to the corresponding acid in liquid phase by means of an oxygen containing gas, such as air, being introduced into the reaction medium or mixture. Generally the oxidation is carried out in the presence of certain heavy metals such as inorganic or organic salts of cobalt, copper, nickel, manganese, silver, vanadium, iron, chromium, etc., that function as oxidation catalysts.

Although liquid phase oxidation of unsaturated aldehydes to the corresponding acids is generally conducted with a metal catalyst, a method is described in U.S. Pat. No. 3,114,769 wherein methacrolein is oxidized to methacrylic acid in the presence of a small quantity of iodine without the addition of a metal catayst. However the liquid phase oxidation of unsaturated aldehydes to the corresponding acids, such as methacrolein to methacrylic acid, has generally been carried out with a metal oxidation catalyst in various inert solvents such as hydrocarbons, chlorinated hydrocarbons, amines, esters, etc. U.S. Pat. Nos. 2,153,406 and 3,155,719 are representative teachings that suggest the use of such solvents including chlorinated solvents such as carbon tetrachloride, chloroform (trichloromethane), ethylene dichloride, and chlorobenzene.

SUMMARY OF THE INVENTION

It is an object of this invention to provide an improved process for the liquid phase oxidation of an unsaturated lower aliphatic aldehyde to the corresponding unsaturated acid, and in particular to accomplish the oxidation of methacrolein to methacrylic acid. Another object of this invention is to carry out the liquid phase oxidation of an unsaturated lower aliphatic aldehyde to the corresponding acid in the absence of an added metal catalyst. It is also an object of this invention to prepare unsaturated lower aliphatic carboxylic acids in high selectivity.

To attain the objects of this invention, a process is provided for oxidizing unsaturated lower aliphatic aldehydes, particularly $\alpha$-$\beta$ unsaturated aldehydes, to the corresponding unsaturated acids wherein the oxidation is carried out by passage of an oxygen-containing gas through a liquid medium containing the unsaturated aldehyde and fluorine-containing organic compound. The essential feature of this process is to conduct the oxidation reaction in the presence of an inert fluorine-containing organic solvent that is in the liquid state during the reaction. The term "inert" means that the solvent is inert under the conditions used. Suitable fluorinated solvents include fluorohydrocarbons, fluoroethers, fluoroalcohols, fluoroketones, fluoroacids and anhydrides, fluoroesters, fluoroamines, and fluoronitriles. Inert co-solvents such as hydrocarbons, halogenated hydrocarbons, ethers, amines, carboxylic acids, and esters are optionally employed.

The reaction is generally conducted in the absence of an added metal oxidation catalyst, but such catalyst may be added to the reaction medium. Although the present process is generally conducted without specifically adding metals, metal ions may be present as impurities in the reactants or introduced by contact of reactants and/or reaction products with the reaction vessel. Therefore, it is advantageous to introduce a chelating agent into the system by conventional means.

DESCRIPTION OF THE INVENTION

The preferred aldehydes used as starting materials in this invention are unsaturated lower aliphatic aldehydes, particularly $\alpha$-$\beta$ unsaturated aldehydes having from 3 to 6 carbon atoms. Such aldehydes include acrolein, methacrolein, crotonaldehyde, alpha-chloroacrolein, beta-ethylacrylic, beta,beta-dimethylacrylic, and 2-hexenal. As specific examples of the aldehydes employed and corresponding acids produced in this invention, acrolein yields acrylic acid, methacrolein yields methacrylic acid, and crotonaldehyde yields crotonic acid.

The oxygen-containing gas employed in carrying out the oxidation is generally oxygen itself or air. Air is included in the term "oxygen-containing gas" as are relatively pure oxygen gas and other oxygen containing gases. If desired, molecular oxygen itself may be diluted with a suitable inert gas such as nitrogen, carbon dioxide or helium.

The oxidation of the unsaturated aldehyde is carried out in a liquid medium in the presence of at least one fluorine-containing organic diluent in the liquid state under reaction conditions where the diluent is a solvent for the unsaturated aldehyde reactant as well as the unsaturated carboxylic acid product. Useful fluorine-containing solvent-diluents include fluorohydrocarbons, fluoroethers, fluoroalcohols, fluoroketones, fluoroacids and anhydrides, fluoroesters, fluoroamines, and fluoronitriles. Generally, the fluorine-containing organic compound will contain from 1 to about 18 carbon atoms and preferably from 1 to 7 carbon atoms. Although a fluorine-containing organic compound having only one fluorine atom is useful in this invention, it is generally desirable, particularly for compounds having two or more carbon atoms, that at least two fluorine atoms be present in the fluorine-containing organic compound. Preferably at least 25% and generally 40% of the replaceable hydrogen atoms of the fluorine-containing organic compound are substituted with fluorine.

Both aliphatic, cycloaliphatic, and aromatic fluorine-containing organic compounds may be employed. Particularly useful fluorohydrocarbons include chlorofluoroalkanes and fluoroalkanes having 1 to 7 carbon atoms and preferably 1 to 3 carbon atoms and most preferably 2 to 3 carbon atoms such as fluorotrichloromethane, monofluoromethane, monofluorodichloromethane, chlorotrifluoromethane, monochlorodifluoromethane, dichlorodifluoromethane, difluoromethane, trifluoromethane, tetrafluoromethane, chloropentafluoroethane, 1,1,1-trifluoroethane, dichlorodifluoroethylene, dichlorotetrafluoroethane, 1,1,2-trichloro-1,2,2-trifluoroethane and 1,1,2,2,2-pentafluoro-1-chloroethane,, hexafluoroethane, 1,2-dichlorohexafluoropropane, 1,1,3-trifluoropentachloropropane, perfluoropropane 1,1,1-trifluorobutane, 1-chloroperfluoropentane, 1,6-difluorohexane and chloroperfluoroheptane. Higher fluorochloroalkanes and fluoroalkanes include 2,2-difluorooctane, 1,10-difluorodecane, 1,1,1-trifluorododecane and perfluorocetane.

Useful aromatic and cycloaliphatic fluorohydrocarbons include hexafluorobenzene, pentafluorobenzene, chloropentafluorobenzene, 1,2,3,5-tetrafluorobenzene, octafluorotoluene (perfluorotoluene), perfluoro-m-xylene, perfluoro-p-xylene, perfluoro-t-butylbenzene, benzotrifluoride, perfluoroperhydroanthracene, perfluorocyclobutane, perfluorocyclohexane and perfluoromethylcyclohexane. Ethylenically unsaturated fluorine-containing compounds are generally not desirable since they may polymerize during the oxidation reaction.

Fluoroethers that may be employed include perfluorodimethyl ether, perfluorodiethyl ether, $\beta,\beta,\beta$-trifluorodiethyl ether, perfluorobutyltetrahydrofuran, trifluoromethyl perfluorocyclopentyl ether, perfluorodipropyl ether, ethyl perfluoroisobutyl ether, and diperfluorobutyl ether.

Fluoroketones that may be used include perfluoro-2-butanone, trifluoroacetone, trifluoroacetylacetone, hexafluoroacetylacetone, pentafluoroacetone, hexafluoroacetone, difluorotetrachloroacetone, 1,3-dichlorotetrafluoroacetone, pentafluoroethyl ethyl ketone, and perfluoro-2-octanone.

Fluoroesters that may be used include methyl trifluoroacetate, trifluoromethyl trifluoroacetate, 2,2,2-trifluoroethyl trifluoroacetate, pentafluoroethyl trifluoroacetate, methyl perfluoropropionate, methyl heptafluorobutyrate, methyl perfluorobutyrate, methyl perfluorohexanoate, ethyl 7-fluoroheptanoate, methyl perfluorooctanoate, ethyl difluoroacetate, ethyl trifluoroacetoacetate, and phenyl trifluoroacetate.

Useful fluoroamines include trifluoroethylamine, perfluorotrimethylamine, perfluoroethylamine, perfluorotriethylamine, perfluorotributylamine, perfluorocyclohexylamine, octafluorohexane diamine, perfluorooctylamine and pentafluoropyridine.

Useful fluoronitriles include perfluoropropionitrile, pentafluoropropionitrile, perfluorobutyronitrile, perfluoroheptylnitrile, trifluoroacetonitrile, perfluorobenzylnitrile, pentafluorobenzonitrile, and p-fluorobenzonitrile.

The fluorine-containing organic compound may be used as the sole solvent-diluent or together with non-fluorinated solvents or diluents. Suitable inert non-fluorinated co-solvents are those known for liquid phase oxidation of unsaturated aldehydes to unsaturated acids such as hydrocarbons, halogenated hydrocarbons, carboxylic acids, alcohols, ethers, amines, esters, and other inert solvents. Suitable solvents include benzene, toluene, p-xylene, o-xylene, m-xylene, toluene, n-hexane, n-heptane, cyclohexane, ethylcyclohexane, petroleum ether, chlorobenzene, carbon tetrachloride, chloroform, acetone, ethyl acetate, butyl acetate, ethylene diamine, ethanol, propanol, butanol, acetic acid, ethylene glycol, glycerol, furfuryl alcohol, dioxane, and other organic solvents. Mixtures of co-solvents may be used together with one or more fluorine-containing organic compounds. Of course, it is important that the fluorine-containing organic solvent and any co-solvent be in the liquid phase during the reaction. When normally gaseous fluorine-containing organic compounds are used as the solvent such as the fluorinated hydrocarbons and fluorocarbons conventionally used as refrigerants and propellants, they are placed under sufficient pressure to maintain them in the liquid phase.

The reaction is conducted in the liquid phase in which the unsaturated aldehyde is dissolved in the fluorine-containing organic solvent so that the concentration of fluorinated organic solvent in the combined fluorinated solvent-aldehyde mixture is between about 1% and 95% by weight, based on the weight of the mixture. Generally the concentration of fluorinated solvent will range from 5% to 95%, and most preferably from 40% to 90% by weight, based on the weight of the fluorinated solvent-aldehyde mixture. As previously mentioned, co-solvents may be employed together with the fluorinated solvent. For instance, mixtures of n-heptane and a fluorinated solvent, benzene and a fluorinated solvent, and toluene and a fluorinated solvent may be used provided the concentration of the fluorinated solvent is within the aforementioned amount.

The reaction is conducted at a moderate temperature, generally between 0° and 100° C. and preferably from about 15° to 60° C. and under sufficient pressure to maintain a liquid reaction phase. With respect to pressure it is preferable to employ total pressures ranging from 5 to 300 atmospheres. When using a fluorinated solvent which is relatively volatile, elevated pressures will be necessary to insure reaction in the liquid phase. Similarly when more volatile aldehydes are used as reactants, elevated pressures may be necessary to avoid loss of aldehyde through vaporization.

As previously mentioned, the reaction is generally conducted without the addition of a metal catalyst; however, the rate of reaction or conversion may be increased by the use of a conventional metal oxidation catalyst. For example, transition metals such as cobalt salts will result in higher conversions but generally provide lower selectivity. Other metal catalysts that may be used are iron, copper, manganese, and nickel salts such as cobalt naphthenate, cobaltous acetate, manganese oleate, cobalt acetylacetonate, nickel stearate, copper butyrate and iron naphthenate. However, the employment of such metal catalysts appears to offer more disadvantage than advantage since the higher conversion advantage is offset by the lower selectivity.

To optimize selectivity, the process should be carried out without adding metallic compounds having a catalytic effect under the reaction conditions; however, in reactions of this type it is frequently possible for metal compounds to be inadvertently present. For example, metal compounds may be present in trace amounts in the starting materials or they may be introduced on contact of the reactants or reaction products with the reaction vessel. Therefore, it is advantageous to employ a chelating agent. The chelating agent may be employed by coating the reactor walls prior to charging reactants or by adding it to the reaction medium. Suitable chelating agents are, for example, polyphosphates such as alkali metal pyrophosphates like sodium pyrophosphate; amino carboxylic acids and their derivatives, such as ethylenediaminetetra-acetic acid and salts thereof such as the sodium salt; nitrilotriacetic acid and its derivatives; 1,2-diamino cyclohexane tetra-acetic acid and its derivatives; hydroxyethyl derivatives of aminotriacetic acid; nitrogen-containing heterocyclic compounds such as α,α'-dipyridyl and dipicolinic acid; organic phosphates and phosphites such as n-octyl phosphate and triphenyl phosphite; hydroxy carboxylic acids such as citric, glyconic and tartaric; 1,3-diketones such as acetylacetone; polyamines such as ethylenediamine; and Schiff's bases such as disalicyladehyde ethylenediamine.

Because higher selectivities are obtained in the absence of metallic compounds having catalytic activity under reaction conditions, it would also be desirable to use in the reaction apparatus that is unlikely to introduce such compounds into the reaction mixture. Thus the apparatus may be titanium, stainless steel, glass, glass-lined, or aluminum. In addition, the walls of the reaction vessel may be pretreated with a chelating agent.

The reaction time is generally less than 10 hours and may be from 30 minutes or longer.

The resulting unsaturated acid which is the product of this process can be recovered by any conventional process, for example, by distillation. Although conventional polymerization inhibitors such as hydroquinone, butylhydroquinone, 2,5-di-tert-amylhydroquinone, 2,6-di-tert-butyl-4-methylphenol, t-butyl hydroquinone, 2,5-di-tert-butylhydroquinone, pyrogallol, sulfur, metallic copper, cuprous chloride, etc., are unnecessary during the course of the reaction, it is preferable to employ a polymerization inhibitor in any subsequent recovery step. If distillation is employed, the distillation should preferably be conducted under subatmospheric conditions to avoid polymerization.

The process may be operated either batchwise or continuously and various forms of continuous operation are possible. The unsaturated acids produced by this invention as well as the esters, i.e., methyl methacrylate, have numerous well known commercial uses; for example, as monomers in the production of synthetic resins and plastic materials.

The invention is illustrated further by means of the following examples wherein percentages are in terms of percent by weight. In the following examples, % Conversion = (Mols Aldehyde Consumed/Mols Aldehyde Charged) × 100, and
% Selectivity = (Mols Acid Produced/Mols Aldehyde Consumed) × 100.

EXAMPLE 1

A cylindrical glass reactor having a 240 ml. capacity was coated with sodium pyrophosphate by washing with 2.5% aqueous sodium pyrophosphate solution and drying in an oven. Into this reactor, there was placed 2 g. of methacrolein and 8 g. of dichlorotetrafluoroethane. The solution was stirred with a magnetic stirring bar, at ambient temperature (25° C.) and under 100 psi of oxygen pressure for 4 hours. After cooling the solution by a Dry Ice - isopropyl alcohol bath, the pressure was slowly vented. To prevent polymerization of methacrolein during recovery, 0.1 g. of 2,6-di-tert-butyl-4-methylphenol was added. Analysis of the solution by gas chromatography (G.C.) showed 100% selectivity to methacrylic acid at 8% conversion of methacrolein.

In a comparative run the procedure was repeated except that n-heptane was employed as the sole solvent in place of the dichlorotetrafluoroethane. Analysis showed a 55% conversion of methacrolein and a 34% selectivity to methacrylic acid.

EXAMPLE 2

The above example was repeated, but the reaction time was extended from 4 to 6 hours. Analysis of the solution by gas chromatography showed that methacrylic acid was obtained in 91% selectivity at 17% conversion of methacrolein.

EXAMPLE 3

Example 1 was repeated, but two fluorine-containing organic solvents were used, 4 g. of perfluorobutyltetrahydrofuran, and 4 g. of hexafluorobenzene. Analysis by gas chromatography showed a 98% selectivity to methacrylic acid with a 23% conversion of methacrolein.

EXAMPLE 4

In a glass lined autoclave, there was placed 35.68 g. of methacrolein, 80 ml. of dichlorodifluoromethane, and 1 ml. of 2.5% aqueous sodium pyrophosphate. The mixture was stirred at ambient temperature (21° C.) and under 175 psi of oxygen pressure for 4 hours. After venting the pressure, 0.1 g. of 2,6-di-tert-butyl 4-methylphenol and 35 g. of n-heptane were added. Gas chromatography analysis showed 83% selectivity of methacrylic acid at 16% conversion of methacrolein.

EXAMPLES 5-8

The following Examples 5 through 8 were carried out using a glass reactor having a 30 ml. capacity, but otherwise the materials and procedures of Example 1 with the exception that 30% by weight of methacrolein (2 g.) in the selected solvent system (4.5 g.) indicated below in Table I were used:

TABLE I

| Example No. | Solvent | Temp. °C. | Conversion of Methacrolein (%) | Selectivity of Methacrylic Acid (%) |
|---|---|---|---|---|
| 5 | dichlorotetrafluoroethane | 26–30 | 25 | 93 |
| 6 | dichlorotetrafluoroethane (2.25 g.) and n-heptane (2.25 g.) | 26–31 | 25 | 94 |
| 7 | dichlorotetrafluoroethane (1.0 g.) and n-heptane (3.5 g.) | 25–31 | 20 | 79 |
| 8 | trichlorotrifluoroethane | 27–28 | 24 | 71 |

EXAMPLES 9-13

The following Examples 9 through 13 were carried out in a 500 cc. autoclave using 200 g. of feed containing 30 weight percent of methacrolein and 70 weight percent of fluorine-containing solvent with the exception that Example 11 was carried out employing a solvent containing perfluoromethylcyclohexane and 1,1,2-trichlorotrifluoroethane in a weight ratio of 5 to 9. Example 12 was carried out in a solvent containing perfluorotoluene and 1,1,2-trichlorotrifluoroethane in a weight ratio of 5 to 9. The mixture was stirred at the temperature indicated under 1000 psi of air pressure for 4 hours. The temperature employed in the reaction, the conversion of methacrolein, and the selectivity of methacrylic acid is indicated in Table II.

TABLE II

| Run No. | Solvent | Temp. °C. | Conversion of Methacrolein (%) | Selectivity of Methacrylic Acid (%) |
|---|---|---|---|---|
| 9 | 1,1,2-trichlorotrifluoroethane | 35 | 28 | 78 |
| 10 | 1,2-dichlorohexafluoropropane | 35 | 28 | 72 |
| 11 | perfluoromethylcyclohexane/1,1,2-trichlorotrifluoroethane (5:9 wt. ratio) | 35 | 22 | 91 |
| 12 | perfluorotoluene/1,1,2-trichlorotrifluoroethane (5:9 wt. ratio) | 35 | 28 | 84 |
| 13 | methyltrifluoroacetate | 35 | 30 | 69 |

EXAMPLES 14-18

The following Examples 14 through 18 were carried out using a glass reactor having a 15 ml. capacity and 6.5 g. of feed containing 30 weight percent of aldehyde and 70 weight percent of fluorine-containing solvent. The particular aldehyde employed is indicated in Table III. The solution was stirred at the temperature indicated under 200 psi of oxygen pressure for 4 hours. The temperature employed in the reaction, the conversion of aldehyde, and the selectivity to the corresponding acid is indicated in Table III. The aldehyde employed in Examples 15 and 16 was acrolein which oxidizes to acrylic acid. The aldehyde employed in Examples 17 and 18 is crotonaldehyde which on oxidation yields crotonic acid.

TABLE III

| Run No. | Aldehyde | Solvent | Temp. °C. | Conversion of Aldehyde (%) | Selectivity of Corresponding Acid (%) |
|---|---|---|---|---|---|
| 14 | methacrolein | pentafluoropyridine | 35 | 7 | 84 |
| 15 | acrolein | 1,1,2-trichlorotrifluoroethane | 25 | 6 | 72 |
| 16 | acrolein | 1,1,2-trichlorotrifluoroethane | 35 | 36 | 53 |
| 17 | crotonaldehyde | hexafluorobenzene | 35 | 79 | 86 |
| 18 | crotonaldehyde | 1,1,2-trichlorotrifluoroethane | 35 | 81 | 87 |

In a comparative run the procedure of Examples 5-8 was repeated except that n-heptane (4.5 g.) was employed as the sole solvent at a temperature ranging between 28° and 30° C. Analysis showed a 28% conversion of methacrolein and a 56% selectivity to methacrylic acid.

COMPARATIVE EXAMPLES A-C

The following runs (A-C) were carried out using a glass reactor having a 30 ml. capacity, but otherwise the materials and procedures of Example 1 with the exception that 50% by weight methacrolein (2 g.) in the selected solvent (2 g.) indicated below in Table IV were used.

TABLE IV

| Run No. | Solvent | Temp. °C. | Conversion of Methacrolein (%) | Selectivity of Methacrylic Acid (%) |
|---|---|---|---|---|
| A | dichlorotetrafluoroethane | 27 | 31 | 76 |
| B | n-heptane | 24 | 37 | 37 |
| C | carbon tetrachloride | 26 | 34 | 33 |

The reaction was run for a time of 4 hours at ambient temperature.

From the above it can clearly be seen that the use of the fluorine-containing organic solvent of Run A dramatically increased the selectivity to methacrylic acid. Without being bound by a particular theory to account for the improved results of a fluorine-containing organic solvent, it may be that the use of a fluorinated organic solvent contributes to greater solubility of oxygen in the solvent and that the fluorinated solvent itself inhibits polymerization of the unsaturated starting material and product.

It is to be understood that the foregoing examples are illustrative only and that the process described in the examples may be modified as will occur to those who are skilled in the oxidation field.

We claim:

1. In a liquid phase oxidation process for oxidizing an α,β-ethylenically unsaturated lower aliphatic aldehyde in an organic solvent to the corresponding unsaturated carboxylic acid by contacting said aldehyde with an oxygen-containing gas, the improvement of conducting the oxidation in the presence of a fluorine-containing organic solvent containing from 1 to about 18 carbon atoms that is in the liquid phase during the oxidation reaction.

2. The process according to claim 1 wherein said unsaturated lower aliphatic aldehyde contains from 3 to 6 carbon atoms.

3. The process according to claim 1 wherein said aldehyde is methacrolein and said acid is methacrylic acid.

4. The process according to claim 1 wherein said fluorine-containing organic solvent contains from about 1 to 7 carbon atoms.

5. The process according to claim 1 wherein said fluorine-containing organic solvent is selected from the group consisting of fluorohydrocarbons, chlorofluorohydrocarbons, fluoroethers, fluoroesters and fluoroamines.

6. The process according to claim 5 wherein said chlorofluorohydrocarbons are chlorofluoroalkones having up to three carbon atoms.

7. The process according to claim 5 wherein said fluorine-containing organic solvent contains from about 1 to 7 carbon atoms.

8. The process according to claim 1 wherein the oxidation reaction is conducted in the presence of a fluorine-containing organic solvent and a non-fluorinated co-solvent.

9. In a liquid phase oxidation process for oxidizing an α,β-ethylenically unsaturated lower aliphatic aldehyde in an organic solvent to the corresponding unsaturated carboxylic acid by contacting said aldehyde with an oxygen-containing gas, the improvement of conducting the oxidation in the presence of a fluorochloroalkane having from 1 to 3 carbon atoms that is in the liquid phase during the oxidation reaction.

10. In a liquid phase oxidation process for oxidizing methacrolein to methacrylic acid in an organic solvent by contacting said methacrolein with an oxygen-containing gas, the improvement of conducting the oxidation in the presence of a fluorochloroalkane having 2 or 3 carbon atoms that is in the liquid phase during the oxidation reaction.

11. The process of claim 10 wherein the oxidation process is conducted without the addition of a metal catalyst.

12. In a liquid phase oxidation process for oxidizing an α,β-ethylenically unsaturated lower aliphatic aldehyde having from 3 to 6 carbon atoms in an organic solvent to the corresponding unsaturated carboxylic acid by contacting said aldehyde with an oxygen-containing gas, the improvement of conducting the oxidation in the presence of a fluorine-containing organic solvent that is in the liquid phase during the oxidation reaction, said solvent containing from 1 to about 18 carbon atoms and having at least 25 percent of the replaceable hydrogen atoms substituted with fluorine.

13. The process according to claim 12 wherein said fluorine-containing organic solvent has at least 40 percent of the replaceable hydrogen atoms substituted with fluorine.

14. The process according to claim 13 wherein said fluorine-containing organic solvent contains from about 1 to 7 carbon atoms.

15. The process according to claim 12 wherein said flourine-containing organic solvent contains from about 1 to 7 carbon atoms.

* * * * *